United States Patent [19]

Pfeiler

[11] 4,368,536

[45] Jan. 11, 1983

[54] DIAGNOSTIC RADIOLOGY APPARATUS FOR PRODUCING LAYER IMAGES

[75] Inventor: Manfred Pfeiler, Erlangen, Fed. Rep. of Germany

[73] Assignee: Siemens Aktiengesellschaft, Berlin & Munich, Fed. Rep. of Germany

[21] Appl. No.: 208,437

[22] Filed: Nov. 19, 1980

[30] Foreign Application Priority Data

Dec. 17, 1979 [DE]  Fed. Rep. of Germany ....... 2950819

[51] Int. Cl.³ .............................................. G03B 41/16
[52] U.S. Cl. ........................................ 378/19; 378/99
[58] Field of Search .................................. 378/19, 99

[56] References Cited

U.S. PATENT DOCUMENTS 4,021,673  5/1977  Bossaert ........................ 250/445 T
4,193,001  3/1980  Liebetruth ..................... 250/445 T Primary Examiner—Craig E. Church
Attorney, Agent, or Firm—Hill, Van Santen, Steadman, Chiara & Simpson

[57] ABSTRACT

In an exemplary embodiment, a measuring arrangement comprised of a radiation source irradiates the radiography subject with a fan-shaped x-ray beam. The output signals of the detectors of the radiation receiver control a video unit via a transmission network. The video unit is designed in the manner of a radar video unit in which a number of concentric image point circles is recorded, each of which is locally allocated to a specific detector in the radiation receiver via the transmission network and is modulated in its intensity largely corresponding to the output signal of the associated detector. The recording operation on the viewing screen of the video unit is synchronized with the scan movement of the measuring arrangement.

1 Claim, 1 Drawing Figure

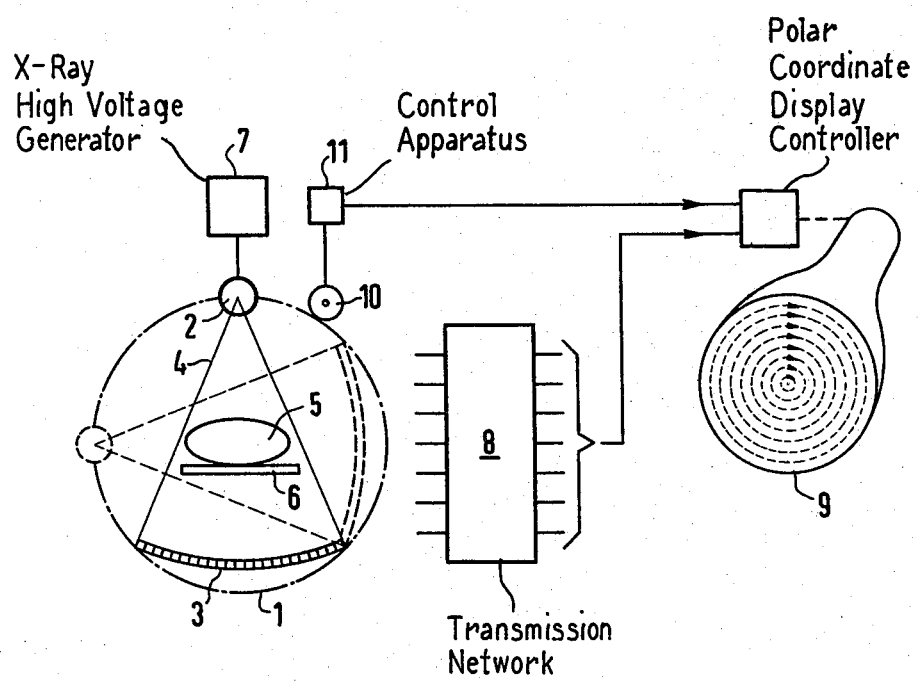

DIAGNOSTIC RADIOLOGY APPARATUS FOR PRODUCING LAYER IMAGES

BACKGROUND OF THE INVENTION

The invention relates to a diagnostic radiology apparatus for producing layer images of a radiography subject, comprising a patient support, a measuring arrangement including a radiation source for irradiating the radiography subject from various directions, the radiation source providing a fan-shaped radiation beam penetrating the layer to be examined, whose extent perpendicular to the layer plane is approximately equal to the layer thickness, and also including a radiation receiver comprised of a series of detectors, which delivers electric output signals corresponding to the measured radiation intensity, a rotating frame on which the radiation source and the radiation receiver are mounted, and a measured value converter with a display unit, for converting the output signals of the radiation receiver into an image of the examined layer.

A diagnostic radiology apparatus of this type, a so-called computer tomograph, is described, for example, in the German OS No. 27 41 732 (U.S. Pat. No. 4,193,001 issued Mar. 11, 1980). The patient is here irradiated from different projections. A computer calculates, from the output signals of the radiation receiver, the attenuation values of specific image points arranged in a matrix. Thus, in the case of the known computer tomograph, one data set is produced per projection. In the computer, after a preprocessing operation, which, in addition to calibration also provides the logrithmation, every data set is subjected to a convolution calculation and then projected back; i.e., added into an image matrix as an addition which, at the end of a scan cycle, and hence also of a computer run, contains the attenuation values of the image points. These attenuation values can then be reproduced optically on a display unit.

If, in the case of the known computer tomograph, a detector, with regard to its transient response, exhibits a deviation from the transient response of the other detectors, then, by means of the latter detector, not the correct value, corresponding to its beam path in the fan-shaped beam configuration, but a false value, is projected into the image matrix. Since the beam path associated with the detector is always the tangent of a circle which is concentric relative to the system center, erroneous information is also circularly built up in the image matrix. Due to the convolution the erroneous signals also have a slight effect on the detector-output signals associated with adjacent beam paths. Thus, in the case of a defective detector element, circular artifacts appear in the image, whereby the connecting line: focus-detector element—projected into the image—is the tangent of a circle.

SUMMARY OF THE INVENTION

The object underlying the invention resides in producing a tomograph of the type initially cited wherein, in the case of a defective detector element, the formation of circular image artifacts is avoided.

This object is achieved in accordance with the invention in that the video unit is designed in the manner of a radar video unit in which a number of concentric image point circles is recorded, each of which is locally allocated to a specific detector in the radiation receiver via a transmission network and is modulated in its intensity largely corresponding to the output signal of the associated detector, and that means are present for synchronizing the recording operation with the scanning movement of the measuring arrangement such that the circles are completely written when a scanning cycle is terminated. Basically all detectors can participate in the intensity modulation of an image circle. The weighting in accordance with a reconstruction algorithm proceeds by means of the transmission network. In the inventive tomograph, the signal issuing from a detector, with omission of the previously described back-projection, is supplied to a reproduction apparatus which does not reproduce the images, read-out from a Cartesian-oriented image matrix, in accordance with the conventionally applied television standard (line-by-line image representation), but, on the contrary, like the video unit of a radar apparatus, builds up the image from concentric circles. A detector is here associated with every circle. It is also possible here to integrate a group of circles and to commonly associate this group with a detector. Signal influences on adjacent circles, or the influencing of an arc length on a circle through an instantaneous signal can be determined by means of analog- or digital-functioning filters in the transmission network. The transmission network contains no image memory as in the case of the known computer tomographs with the initially described back-projection into an image matrix.

The transmission network connects the measuring arrangement comprised of the X-ray source and the radiation receiver on line with the video unit. A continuous fluoroscopy is thereby also possible.

The invention shall be explained in greater detail in the following on the basis of an exemplary embodiment illustrated in the drawing; and other objects, features and advantages will be apparent from this detailed disclosure and from the appended claims.

BRIEF DESCRIPTION OF THE DRAWING

The single FIGURE is a diagrammatic illustration of a tomographic system in accordance with the present invention.

DETAILED DESCRIPTION

In the drawing a rotating frame 1 is illustrated on which a measuring arrangement, comprised of an X-ray tube 2 and a radiation receiver 3, is mounted. The X-ray tube 2 emits a fan-shaped X-ray beam 4 which entirely penetrates a transverse layer of a patient 5. The patient 5 is supported on a patient support 6. The thickness of the radiation beam 4 perpendicular to the layer plane is equal to the layer thickness. The X-ray tube 2 is fed by an X-ray generator 7, whereas the radiation receiver 3, comprised of a series of detectors, for example 512 detectors, is connected to a transmission network 8 which exhibits, for every detector, one input channel and one output channel. The reproduction of the image of the examined transverse layer of the patient 5 proceeds on the video unit 9.

For scanning the patient 5 the rotating frame 1 with the X-ray tube 2 and the radiation receiver 3 is rotated at least 360° about the patient 5 by means of a rotational drive device 10. The rotating device 10 is connected to a control apparatus 11.

The video unit 9 is designed in the manner of a radar video unit; i.e., on its viewing screen, by means of an electron beam (which rotates about a center point in synchronism with an image rate and is deflected radially in synchronism with a line scan rate), a number of concentric image point circles is written, each of which is allocated, via the transmission network 8, to a specific detector in the radiation receiver 3 and is modulated in its intensity largely corresponding to the output signal of the associated detector. The control apparatus 11 effects a synchornization of the scanning movement of the measuring arrangement 2, 3 with the recording operation on the video unit 9, so that the circles on the viewing screen of the video unit 9 are completely recorded when a scan cycle; i.e., a rotation of the measuring arrangement 2, 3 through 360°, is terminated.

Since the video unit 9 is connected on line to the radiation receiver 3 via the transmission network 8, it is possible to conduct a fluoroscopy through continuous rotation of the measuring arrangement 2, 3.

It will be apparent that many modifications and variations may be effected without departing from the scope of the novel concepts and teachings of the present invention.

SUPPLEMENTAL DISCUSSION

Convention image reconstruction in computer tomography with fan-beam scanning, is explained, for example in an article by Schwierz, Härer and Rührnschopf entitled "Principles of Image Reconstruction in X-Ray Computer Tomography", Siemens Forsch.-u. Entwickl.-Ber., Volume 7, (1978), No. 4.

Specific circuitry for the accumulation of detector outputs and their transmission via a multiplexer are disclosed, for example, in U.S. Pat. No. 4,135,247 issued Jan. 16, 1979.

With the transmission network 8 of the illustrated embodiment, the conventional back projection step is omitted, and for each x-ray pulse, the signal from each detector, after amplification, and other desired processing, may be sampled in step with the scanning of a diametric line on the display screen 9 by means of a conventional multiplex circuit such as shown in U.S. Pat. No. 4,135,247.

In this example, the elements of detector 3 may be designated in series from left to right as viewed in the drawing, as detector elements 3-1 through 3-512. With respect to a symmetry line from the X-ray focus and extending through the center of rotation of frame 1, the detector elements 3 may be offset so that each detector scans a different radius about the center of frame rotation. In this case, for example, detector 3-1 at the extreme left may scan about a maximum radius (R1), while detector 3-512 may scan at a slightly lesser radius (R512). Thus for each projection, the beam of display 9 would begin a scan at one extreme of a diametric scan line and record the value from detector 3-1, with the successive detector outputs 3-2 et seq being supplied as the beam scans to the opposite extreme of the diametric scan line. In this way, a partial image field would be traced by the beam in each 180° of rotation of the beam and of frame 1. With a complete 360° rotation of the frame 1, two interleaved image fields will have been traced on the display screen, with points of radius R1 from the center of rotation of frame 1, recorded along a circle of maximum radius on the display screen, and with points of radius R512 recorded along a circle of slightly lesser radius and so on.

For the illustrated example, the transmission network 8 may be carried on the rotating frame 1. For the case of continuous rotation, a multiplexer carried on frame 1, may supply the output signals from transmission network 8 to a light emitting device on the frame 1, which is coupled throughout its circular path with a stationary optical conductor in the form of a ring. The optical conductor is provided with a coupling gap for supplying the multiplexed light signals via an optical-electric transducer to the beam intensity control electrode of the display device 9.

It is evident that the multiplex control circuitry may be carried on the frame 1 and be synchronized with the pulsing operation of X-ray source 2 in the same way as for U.S. Pat. No. 4,135,247. With the transmission network 8, however, analog to digital conversion may be omitted and the detector signals transmitted via 512 analog channels including suitable amplification and convolution filtering in analog form, prior to a reset integrator for each channel and the analog multiplexer. Thus in this example, for each pulse of the X-ray source 2, the detector outputs are transmitted via respective analog channels permanently assigned to the respective detector elements, so that transient response compensation, calibration, correction and convolutional filtering may be applied in analog form during the on-line transmission of the detector outputs to the display device for essentially simultaneous display of the processed detector signals. As previously mentioned, conventional digital filtering is an alternative.

To facilitate continuous rotation of the frame 1 at a rate to avoid flicker on the display 9, the x-ray high voltage generator 7 may also be carried on frame 1 and may receive alternating current at power frequency, or at a medium frequency of one to five kilohertz via a rotary transformer coupling, or via slip rings or the like. For background concerning continuously rotating fan-beam scanners, reference may be made to the following published German applications:

German application No. P 28 46 526.1 filed Oct. 25, 1978 (U.S. Ser. No. 078,052 filed Sept. 24, 1979, and allowed Aug. 7, 1980, Attorney Case No. P-79,1152, Applicant Ref. VPA 78 P5114)

German application No. P 28 55 379.5 filed Dec. 21, 1978 U.S. Ser. No. 094,766 filed Nov. 16, 1979, Attorney Case No. P-79,1089, Applicant Ref. VPA 78 P5139)

I claim as my invention:

1. Diagnostic radiology apparatus for producing layer images of a radiography subject, comprising a patient support, a measuring arrangement for irradiating the radiography subject from various directions, comprised of a radiation source (2) which emits a fan-shaped radiation beam penetrating the layer to be examined, whose dimension perpendicular to the layer plane is approximately equal to the layer thickness, and of a radiation receiver (3) formed of a series of detectors, which delivers electric output signals corresponding to the measured radiation intensity, a rotating frame (1) on which the radiation source and the radiation receiver are mounted, and a transmission network (8) with a video unit (9) for converting the output signals of the radiation receiver into an image of the examined layer, the video unit (9) being operable with a polar coordinate system in which a number of concentric image point circles are written, each of which is locally allocated, via the transmission network (8), to a specific detector in the radiation receiver (3) and is modulated in its intensity largely corresponding to the output signal of the associated detector, and means (11) for synchronizing the recording operation of the video unit with the scanning movement of the measuring arrangement (2, 3) such that the circles are completely recorded when a scan cycle is terminated.

* * * * *